US012748050B2

(12) United States Patent
Lin

(10) Patent No.: US 12,748,050 B2
(45) Date of Patent: Sep. 29, 2026

(54) MID-INFRARED WAVEGUIDE SENSORS FOR VOLATILE ORGANIC COMPOUNDS

(71) Applicant: The Texas A&M University System, College Station, TX (US)

(72) Inventor: Pao Tai Lin, College Station, TX (US)

(73) Assignee: The Texas A&M University System, College Station, TX (US)

( * ) Notice: Subject to any disclaimer, the term of this patent is extended or adjusted under 35 U.S.C. 154(b) by 139 days.

(21) Appl. No.: 18/927,314

(22) Filed: Oct. 25, 2024

(65) Prior Publication Data

US 2025/0044226 A1 Feb. 6, 2025

Related U.S. Application Data

(63) Continuation of application No. 18/089,872, filed on Dec. 28, 2022, now Pat. No. 12,152,986, which is a continuation of application No. 16/589,818, filed on Oct. 1, 2019, now Pat. No. 11,561,172.

(60) Provisional application No. 62/739,610, filed on Oct. 1, 2018.

(51) Int. Cl.
*G01N 21/59* (2006.01)
*G01N 33/00* (2006.01)

(52) U.S. Cl.
CPC ......... *G01N 21/59* (2013.01); *G01N 33/0004* (2013.01); *G01N 33/0047* (2013.01); *G01N 33/0062* (2013.01); *G01N 2201/08* (2013.01)

(58) Field of Classification Search
None
See application file for complete search history.

(56) References Cited

U.S. PATENT DOCUMENTS

| | | | | |
|---|---|---|---|---|
| 3,781,748 A * | 12/1973 | Bishop | ...................... | G01J 5/20 374/129 |
| 5,629,953 A * | 5/1997 | Bishop | ...................... | H01S 3/17 372/39 |
| 6,496,636 B1 | 12/2002 | Braiman et al. | | |
| 7,559,594 B2 | 7/2009 | Mcmillen | | |
| 7,724,997 B2 | 5/2010 | Kittaka et al. | | |
| 9,709,504 B2 | 7/2017 | Osterlund et al. | | |
| 10,591,410 B2 | 3/2020 | Lin | | |

(Continued)

FOREIGN PATENT DOCUMENTS

| | | | |
|---|---|---|---|
| JP | 58021211 A * | 2/1983 | ........... G02B 6/1245 |
| WO | WO-2009131535 A1 * | 10/2009 | ........... G01N 21/552 |

OTHER PUBLICATIONS

"U.S. Appl. No. 16/179,470, Examiner Interview Summary mailed Dec. 18, 2019", 4 pgs.

(Continued)

*Primary Examiner* — Marcus H Taningco
(74) *Attorney, Agent, or Firm* — Schwegman Lundberg & Woessner, P.A.

(57) ABSTRACT

Chalcogenide waveguides with high width-to-height aspect ratios and a smooth exposed surfaces can serve as mid-infrared evanescent-absorption-based sensors for detecting and identifying volatile organic compounds and/or determining their concentration, optionally in real-time. The waveguide sensors may be manufactured using a modified sputtering process in which the sputtering target and waveguide substrate are titled and/or laterally offset relative to each other and the substrate is continuously rotated.

20 Claims, 8 Drawing Sheets

(56) References Cited

U.S. PATENT DOCUMENTS

| | | | | |
|---|---|---|---|---|
| 2004/0240822 | A1 | 12/2004 | Patel et al. | |
| 2006/0228064 | A1 | 10/2006 | Hunt et al. | |
| 2008/0192332 | A1* | 8/2008 | Sanghera | H01S 3/0632 359/333 |
| 2009/0041405 | A1 | 2/2009 | Dai et al. | |
| 2010/0096255 | A1* | 4/2010 | Ye | H01J 37/32706 204/192.15 |
| 2011/0090484 | A1 | 4/2011 | Oesterlund et al. | |
| 2011/0217001 | A1 | 9/2011 | Rochette et al. | |
| 2011/0311180 | A1 | 12/2011 | Hu et al. | |
| 2013/0142477 | A1 | 6/2013 | Diemeer | |
| 2013/0155723 | A1 | 6/2013 | Coleman | |
| 2014/0185042 | A1 | 7/2014 | Baets et al. | |
| 2014/0264030 | A1 | 9/2014 | Lin et al. | |
| 2016/0139335 | A1 | 5/2016 | Abel et al. | |
| 2017/0055906 | A1 | 3/2017 | Bremer | |
| 2017/0082544 | A1 | 3/2017 | Van Dorpe et al. | |
| 2017/0285264 | A1 | 10/2017 | Cote et al. | |
| 2019/0128798 | A1 | 5/2019 | Lin | |
| 2019/0129094 | A1 | 5/2019 | Lin | |
| 2019/0234850 | A1 | 8/2019 | Singh et al. | |
| 2020/0103344 | A1 | 4/2020 | Lin | |
| 2023/0140255 | A1 | 5/2023 | Lin | |

OTHER PUBLICATIONS

"U.S. Appl. No. 16/179,470, Non Final Office Action mailed Sep. 18, 2019", 11 pgs.

"U.S. Appl. No. 16/179,470, Response filed Jan. 21, 2020 to Non Final Office Action mailed Sep. 18, 2019", 8 pgs.

"U.S. Appl. No. 16/179,502, Examiner Interview Summary mailed Nov. 14, 2019", 3 pgs.

"U.S. Appl. No. 16/179,502, Non Final Office Action mailed Aug. 7, 2019", 11 pgs.

"U.S. Appl. No. 16/179,502, Notice of Allowance mailed Nov. 27, 2019", 8 pgs.

"U.S. Appl. No. 16/179,502, Response Filed Nov. 6, 2019 to Non-Final Office Action Mailed Aug. 7, 2019", 9 pgs.

"U.S. Appl. No. 16/589,818, Non Final Office Action mailed May 9, 2022", 8 pgs.

"U.S. Appl. No. 16/589,818, Notice of Allowance mailed Sep. 27, 2022", 7 pgs.

"U.S. Appl. No. 16/589,818, Response filed Apr. 12, 2022 to Restriction Requirement mailed Mar. 16, 2022", 5 pgs.

"U.S. Appl. No. 16/589,818, Response filed Aug. 9, 2022 to Non Final Office Action mailed May 9, 2022", 9 pgs.

"U.S. Appl. No. 16/589,818, Restriction Requirement mailed Mar. 16, 2022", 7 pgs.

"U.S. Appl. No. 18/089,872, Non Final Office Action mailed May 21, 2024", 8 pgs.

"U.S. Appl. No. 18/089,872, Notice of Allowance mailed Oct. 15, 2024", 7 pgs.

"U.S. Appl. No. 18/089,872, Response filed Aug. 21, 2024 to Non Final Office Action mailed May 21, 2024", 8 pgs.

Chen, Li, et al., "12.5 pm/V hybrid silicon and lithium niobate optical microring resonator with integrated electrodes", Optics Express 27003, vol. 21, No. 22, (Nov. 2013), 8 pgs.

Jin, Tiening, et al., "Flexible Mid-infrared Aluminium Nitride Waveguides for Real-time and Label-Free Chemical Sensing", SeTu1E.3. Advanced Photonics Congress (IPR, Networks, NOMA, PS, Sensors, SPPCom) OSA, (2017).

Jin, Tiening, et al., "Monolithic Mid-Infrared Integrated Photonics Using Silicon-on-Epitaxial Barium Titanate Thin Films", ACS Appl. Mater. Interfaces, (2017), 21848-21855.

Jin, Tiening, et al., "Monolithically Integrated Si-on-AlN Mid-Infrared Photonic Chips for Real-Time and Label-Free Chemical Sensing", ACS Appl. Mater. Interfaces, vol. 9, (2017), 42905-42911.

Jin, Tiening, et al., "Real-Time and Label-Free Chemical Sensor-on-a-chip using Monolithic Si-on-BaTiO3 Mid-Infrared waveguides", Scientific Reports 7, (2017), 8 pgs.

Lin, Pao, et al., "Label-Free Glucose Sensing Using Chip-Scale Mid-Infrared Integrated Photonics", Adv. Optical Mater, (2016), 1755-1759.

Lin, Pao, "Real-time and label-free chemical sensing using flexible mid-infrared photonic circuits (Conference Presentation)", Proc. SPIE 10662, Smart Biomedical and Physiological Sensor Technology XV, 106620N, (May 2018), 5 pgs.

Ma, Pan, et al., "Low-loss chalcogenide waveguides for chemical sensing in the mid-infrared", vol. 21, No. 24, Optics Express, (2013), 11 pgs.

Rabiei, Payam, et al., "Heterogeneous lithium niobate photonics on silicon substrates", Optics Express 25573, vol. 21, No. 21, (2013), 9 pgs.

Weigel, Peter, et al., "Lightwave Circuits in Lithium Niobate through Hybrid Waveguides with Silicon Photonics", Scientific Reports, (2016), 9 pgs.

* cited by examiner

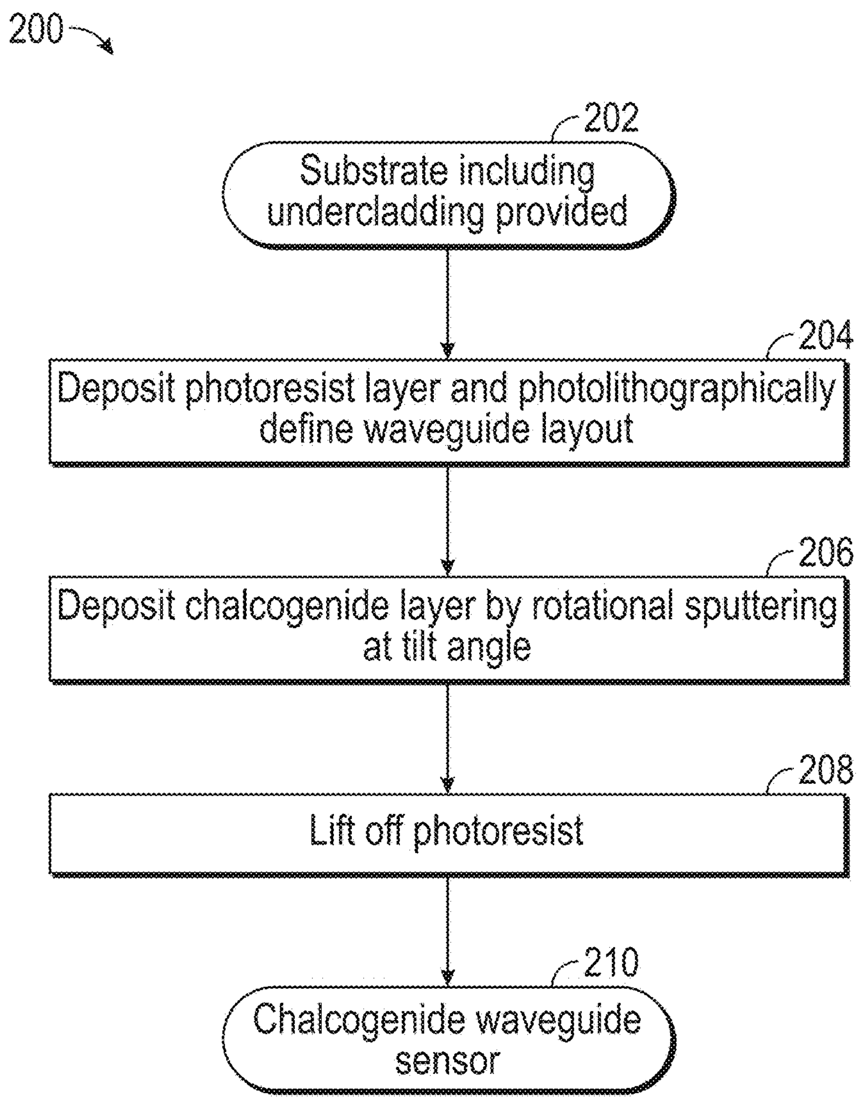
FIG. 2
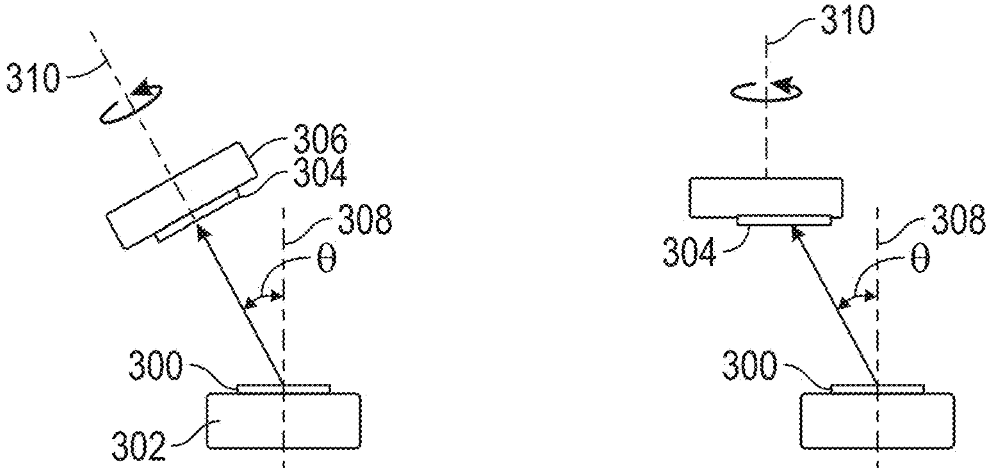
FIG. 3A
FIG. 3B

MID-INFRARED WAVEGUIDE SENSORS FOR VOLATILE ORGANIC COMPOUNDS

PRIORITY

This application is a continuation of U.S. patent application Ser. No. 18/089,872, filed Dec. 28, 2022, which application is a continuation of U.S. patent application Ser. No. 16/589,818, filed Oct. 1, 2019, which application claims the benefit of priority to U.S. Provisional Application Ser. No. 62/739,610, filed Oct. 1, 2018, which are incorporated by reference herein in their entireties.

TECHNICAL FIELD

The present disclosure relates to the detection of volatile organic compounds (VOCs), and more specifically to waveguide-based VOC sensors.

BACKGROUND

VOCs are organic (i.e., carbon-based) chemical compounds that have a high vapor pressure at room temperature, resulting in a low boiling point, which causes large numbers of molecules to evaporate or sublime from the liquid or solid form of the compound and enter into the surrounding air. Although VOCs exist widely throughout our surroundings, they can be damaging to the environment and harmful or even fatal to humans. Exposure to high concentrations of VOCs can, for instance, cause throat irritation, headaches, and internal organ damage, and continuous low-level exposure can have long-term adverse health effects. On the other hand, some VOCs are biomarkers for various diseases and, as such, have been utilized to monitor health conditions. Acetone, for example, is widely used as a biomarker for diabetes since it is found in the exhaled breath of diabetes patients, its concentration being indicative of the patient's glucose level. Accordingly, the detection of VOCs is relevant to human health monitoring as well as tracing environmental toxins.

Currently, the most prevalent method for organic compounds analysis is gas chromatography mass spectrometry. This method uses bulky and expensive instrumentation, and is time-consuming because gas chromatography can take several minutes to separate different gases, which poses a challenge for instantaneous VOC measurements. Another method widely applied in VOC detection relies on electrical resistance changes in metal oxide semiconductor (MOS) sensors in the presence of VOCs due to charge transfer between the sensor surface and the chemisorption oxygen. MOS-based sensors have shown high sensitivity. However, they provide poor selectivity because different VOCs, as well as background gases such as ozone or water, affect the resistance similarly. An alternative, small-scale sensing platform that can achieve real-time VOC detection while retaining high specificity and accuracy is desirable.

SUMMARY

Described herein are waveguide-based sensor devices and systems, along with associated methods of manufacture and use, for the detection and identification of VOCs based on their characteristic "fingerprint" absorptions in the mid-IR wavelength regime, herein understood as the range between 2.5 μm and 15 μm. The operating principle of the sensor devices is the attenuation of an optical mode travelling in the waveguide due to the absorption of the evanescent field by VOC molecules at the waveguide surface. The magnitude of the attenuation is indicative of the VOC concentration, whereas the wavelength dependence of the attenuation allows an inference of the particular kind of VOC being detected. Accordingly, to discriminate between different VOCs, a sensor device in accordance with various embodiments may utilize a tunable mid-IR lights source (e.g., a tunable laser) to measure attenuation at multiple wavelengths or across a continuous wavelength range.

Waveguide-based VOC detection is challenging, in comparison to the waveguide-based sensing of many other chemical or biochemical analytes (which are usually dissolved in liquid samples), due to the typically low concentrations of the VOCs in the gas phase. In accordance with various embodiments, VOC sensing is rendered feasible by a combination of waveguide material, geometric, and surface properties that achieves high sensitivity to VOCs through low-loss light guiding in conjunction with a strong evanescent field. In particular, in preferred embodiments, a chalcogenide, e.g., arsenic triselenide ($As_2Se_3$), is selected as the waveguide material. Chalcogenides provide high mid-IR transparency across a wide wavelength range, and have relatively high refractive indices resulting in a high index contrast with standard oxide undercladdings, allowing for good optical mode confinement and, thus, efficient light guiding. The waveguide geometry features, in preferred embodiments, an upper waveguide surface (meaning the waveguide surface that is exposed to the environment, as distinguished from the waveguide interface with the undercladding) that is free of edges, which substantially diminishing scattering losses, as well as a large width-to-height aspect ratio (e.g., greater than two, preferably greater than five), which results in a strong evanescent field. For example, the waveguide may have a "flattened semielliptical" cross-sectional profile, rather than the common rectangular cross section. Such a rounded, edge-free surface and high aspect ratio can be achieved in the manufacturing process by depositing, following photolithographic definition of the waveguide, the chalcogenide layer on the substrate using a new sputtering process in which the substrate is tilted or offset relative to the sputtering target and rotates continuously. With a chalcogenide waveguide thus manufactured, VOC concentrations of as little as tens of parts per million (ppm) can be detected in some embodiments. Beneficially for many practical sensing applications, waveguide-based sensor devices as described herein are amenable to chip-scale implementations and capable of real-time VOC detection and concentration monitoring.

The foregoing summary introduces various concepts, principles, and aspects of the inventive subject matter, and certain features of various embodiment, but does not exhaustively list all inventive features and aspects, and is not intended to limit the scope of the claimed subject matter in any way.

BRIEF DESCRIPTION OF THE DRAWINGS

Various aspects and example embodiments are described herein with reference to the accompanying drawings, in which:

FIG. 2 is a flow chart of a method of manufacturing a waveguide structure as shown in FIGS. 1A and 1B, in accordance with various embodiments;

FIGS. 3A and 3B are schematic diagrams illustrating sputtering configurations in accordance with various embodiments;

DESCRIPTION

Figure 1A:
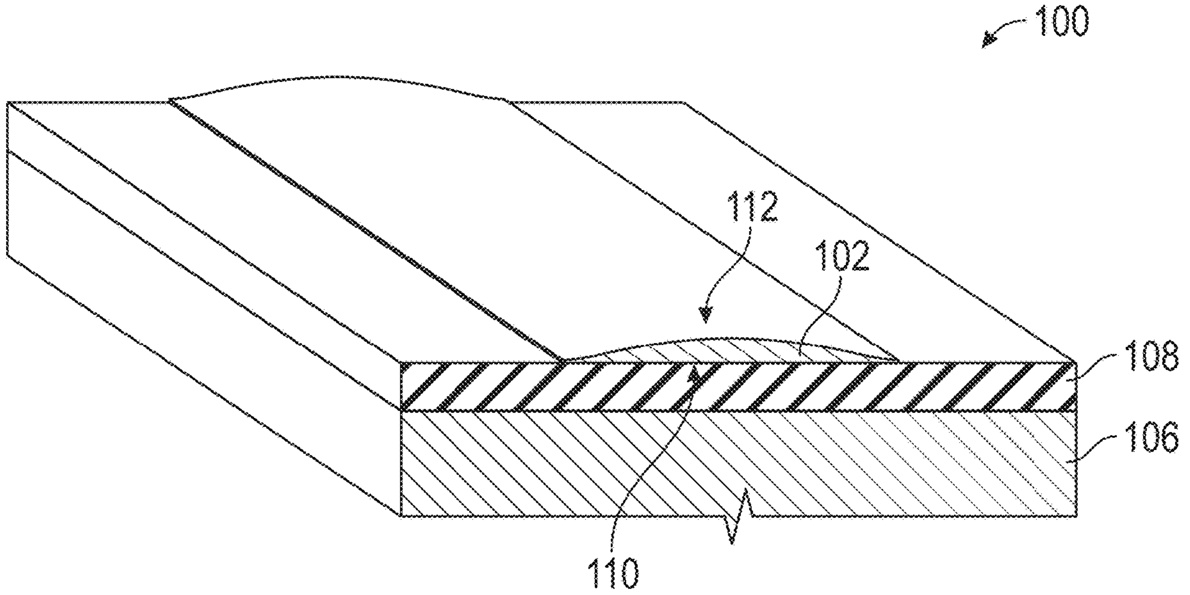
FIGS. 1A and 1B are schematic perspective and cross-sectional views of an example waveguide structure in accordance with various embodiments.
Figure 1B:
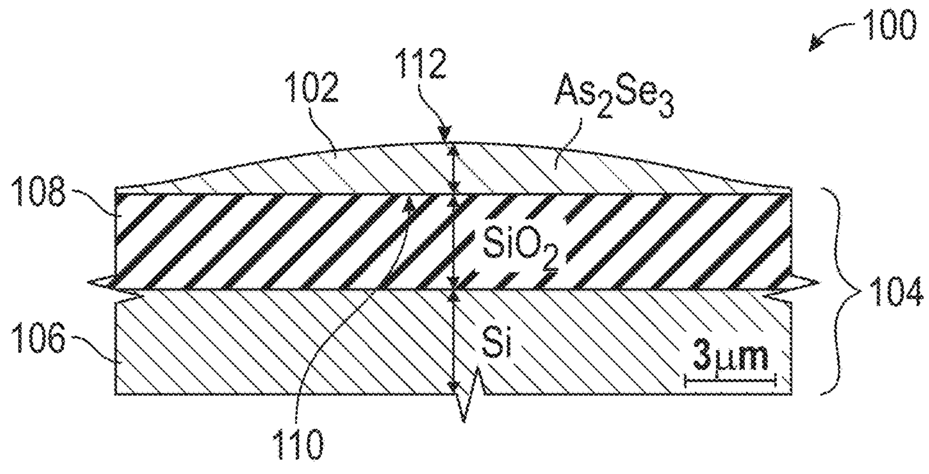

FIGS. 1A and 1B are schematic perspective and cross-sectional views of a waveguide structure 100 as may be used in VOC sensor devices in accordance with various embodiments. The waveguide structure 100 includes a ridge waveguide 102 formed on a substrate 104 that comprises a thick handle 106 for mechanical stability and a thin top layer serving as an undercladding 108 for the ridge waveguide 102. The substrate handle 106 may, for instance, be made from a standard silicon wafer. The undercladding 108 may be an oxide layer (e.g., made of silicon dioxide ($SiO_2$), magnesium oxide (MgO), or aluminum oxide ($Al_2O_3$)) or other dielectric layer (e.g., made of calcium fluoride ($CaF_2$), and may be a few micrometers thick. The waveguide 102 is made, in accordance with various embodiments, from a chalcogenide, i.e., a crystalline or amorphous semiconductor compound including one or more chalcogen elements (e.g., sulfur, selenium, tellurium) covalently bonded to an electropositive element. Beneficially, chalcogenides provide wide windows of infrared transparency (e.g., with at least 50% transmission, at least 70% transmission, or at least 90% transmission), ranging from about 2 μm or less to at least about 10 μm, at least about 15 μm, or even up to about 20 μm, depending on the particular material. In addition, chalcogenides have a suitable index of refraction, e.g., in the range from about 2 to about 3 within the mid-infrared regime; such a relatively high index provides good index contrast to that of the undercladding 108, which is, for $SiO_2$, about 1.45. In one embodiment, the waveguide 102 is made of $As_2Se_3$ glass, which has a refractive index of about 2.79 and is transparent to light from optical wavelengths up to mid-infrared wavelength of about 15 μm. Other suitable chalcogenides include zinc sulfide, arsenic sulfide, antimony sulfide, antimony selenide, etc. The waveguide 102 is directly exposed to the surrounding without any intervening overcladding; it is, thus, usually air-clad during use.

As shown in FIGS. 1A and 1B, the boundaries of the cross-sectional profile of the ridge waveguide 102 are defined by the flat interface 110 with the undercladding 108 and a smooth, rounded top surface 112, corresponding to the surface that will be exposed to the VOC during use. The exposed top surface 112 is free of the sharp corners (in the two-dimensional profile) or edges (in the three-dimensional structure) that are characteristic of conventional rectangular waveguides, where such edges tend to result in significant scattering losses; the absence of edges in the top surface 112 of the waveguide 102, accordingly, contributes substantially to low light propagation losses and, as a consequence, high waveguide sensitivity, as needed for VOC detection at low concentrations. In some embodiments, the waveguide 102 has an approximately semi-elliptical or flattened semi-elliptical profile, although, as shown, the flanks of the waveguide may fall off more gradually than the edges of a true semi-elliptical cross section, preventing a sharp edge at the interface with the undercladding 108. The cross section of waveguide 102 exhibits a high aspect ratio of width to height, e.g., a ratio greater than five in various embodiment, and generally a ration in the range from two to twenty. The waveguide is dimensioned to guide light at wavelengths in the mid-IR regime, and the low waveguide height, compared to the waveguide width, causes a substantial portion of the optical mode (e.g., the fundamental mode) to leak into the surrounding region as an evanescent wave, likewise contributing to high sensitivity. In one example embodiment, the waveguide has a width of about 10 μm (as measured, e.g., between the two points of the profile at which the height is at half the maximum waveguide height) and a (maximum) height of about 1.5 μm.

FIG. 2 is a flow chart of a method 200 of manufacturing a waveguide structure 100 as shown in FIGS. 1A and 1B, in accordance with various embodiments. The method 200 starts, at 202, with a suitable substrate 102, e.g., a silicon wafer with a $SiO_2$ cladding layer (e.g., 3 μm thick) serving as undercladding 108 for the waveguide 102. The waveguide layout is negatively defined on the substrate, in step 204, by depositing a photoresist layer on the undercladding and photolithographically patterning the photoresist layer, as known to those of ordinary skill in the art. The patterned photoresist layer exposes the undercladding in areas where the undercladding will interface with the waveguide, and covers the remaining surface of the undercladding. In one embodiment, negative tone photoresist NR9-3000PY is used in this process. In step 206, a chalcogenide (e.g., $As_2Se_3$) film is deposited over the patterned substrate by sputtering. For example, in one embodiment, a 99.99% $As_2Se_3$ target is radio-frequency sputtered with a power of 40 W. Importantly, in order to obtain an approximately (flattened) semi-elliptical waveguide profile with a smooth, edge-free top surface, the sputtering target and substrate may be tilted with respect to each other (as shown in FIGS. 3A and 3B), rather than being oriented in parallel and directly facing one another as is the case in conventional sputtering. Further, the substrate is continuously rotated during the sputtering process about an axis perpendicular to the substrate. Following deposition of the chalcogenide, the photoresist layer and chalcogenide layer thereabove are removed, in step 208, by a lift-off process, leaving only the chalcogenide waveguide 102 on the undercladding 108, which completes manufacture of the waveguide sensor at 210.

FIGS. 3A and 3B are schematic diagrams of tilted and/or offset sputtering configurations in accordance with various embodiments, illustrating the relative position and orientation of the sputtering target 300 (shown on a target holder 302) and the substrate 304 (shown on a substrate holder 306). The sputtered particles generally emanate from the target 300 anisotropically, with a rotational symmetry about an axis 308 normal to the target and maximum particle density along this axis 308. The anisotropy is exploited, in accordance with various embodiments, to achieve the desired waveguide profile by rotating the substrate 304 about a rotational axis 310 perpendicular to the substrate 302, and tilting and/or laterally off-setting the substrate 304 relative to the target 300. For example, as shown in FIG. 3A, the substrate 304 may be tilted relative to the target 300 by an angle θ enclosed between the axis 308 normal to the target 300 and an axis, such as rotational axis 310, normal to the substrate 304. This tilt angle θ defines the radius and aspect ratio of the waveguide structure, that is, for a semielliptical structure, the lengths of the minor and major axes. Suitable tilt angles θ are in the range from about 15 to about 75 degrees. Alternatively, as shown in FIG. 3B, the substrate 304 may be oriented parallel to the target 300, but positioned with an off-set between its rotational axis 310 and the symmetry axis 308 of the target. The waveguide profile is determined by the combination of tilt angle and off-set.

Rotational sputtering as depicted in FIG. 3 allows manufacturing waveguides with a smooth, extensive top surface and a large width-to-height ratio, both of which are important for achieving increased waveguide sensitivity (as compared with conventional waveguide geometries) to enable VOC detection. In some embodiments, VOC concentrations on the order of only tens of ppm are detectable with waveguide-based sensors as described herein.

Figure 4A:
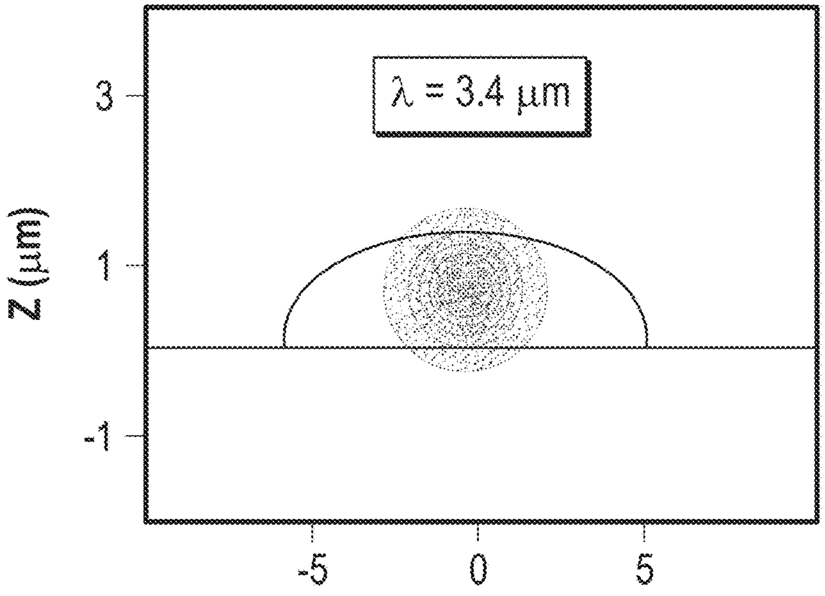
FIGS. 4A and 4B are two-dimensional and one-dimensional optical mode profiles at a mid-infrared wavelength for the waveguide structure of FIGS. 1A and 1B.
Figure 4B:
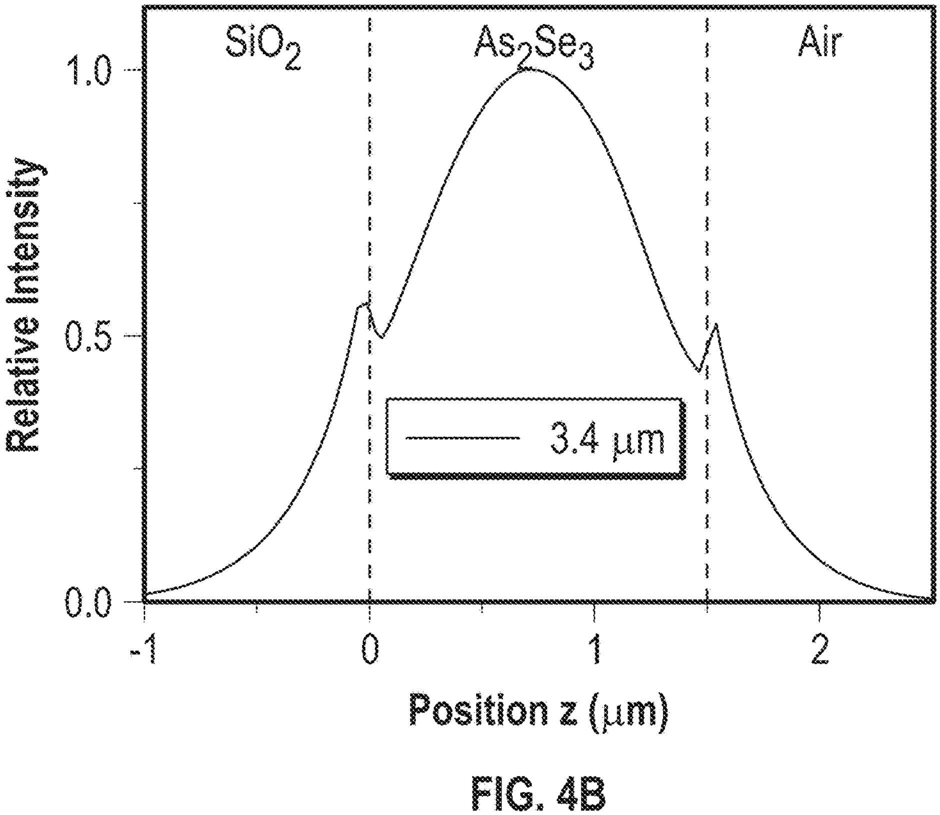

FIGS. 4A an 4B illustrate an infrared optical mode in an example $As_2Se_3$ waveguide (e.g., as depicted in FIGS. 1A and 1B) with a semi-elliptical cross section, 10 μm wide and 1.5 μm thick, on an $SiO_2$ undercladding. The refractive indices of the waveguide and cladding are 2.79 and 1.45, respectively. FIG. 4A displays the two-dimensional optical field, as can be measured or computationally simulated (e.g., with the finite difference method), of the fundamental transverse optical mode excited in the waveguide at a wavelength of 3.4 μm. The mode has a generally ellipsoid (as depicted close to spherical) intensity profile in the waveguide center, and an evanescent field that extends both into the undercladding below ($z \leq 0$) and the air above ($z \geq 1.5$ μm) the $As_2Se_3$ layer. The evanescent field is more easily seen in FIG. 4B, which illustrates the one-dimensional intensity profile of the fundamental optical mode along the z axis. As shown, at a distance of 0.5 μm from the exposed waveguide surface, the intensity of the evanescent wave is still above about 10% of the peak intensity of the optical mode in the chalcogenide waveguide. The evanescent field intensity determines the sensitivity of the sensor to VOCs. Due to the high y:z aspect ratio (y being the width dimension of the waveguide), the evanescent field is much stronger in the z direction than in the y direction; therefore, a transverse magnetic (TM) polarization is applied in the simulation. Further, as comparative simulations and measurements at different wavelengths have shown, the evanescent field becomes stronger towards longer wavelengths.

Figure 5A:
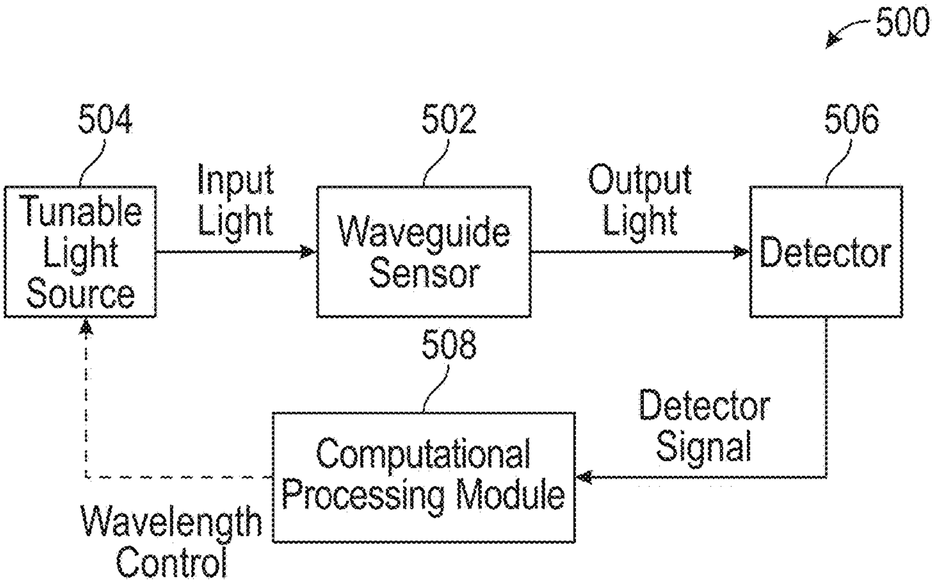
FIGS. 5A and 5B are block diagrams of chemical sensing systems incorporating the waveguide structure of FIGS. 1A and 1B, in accordance with various embodiments.
Figure 5B:
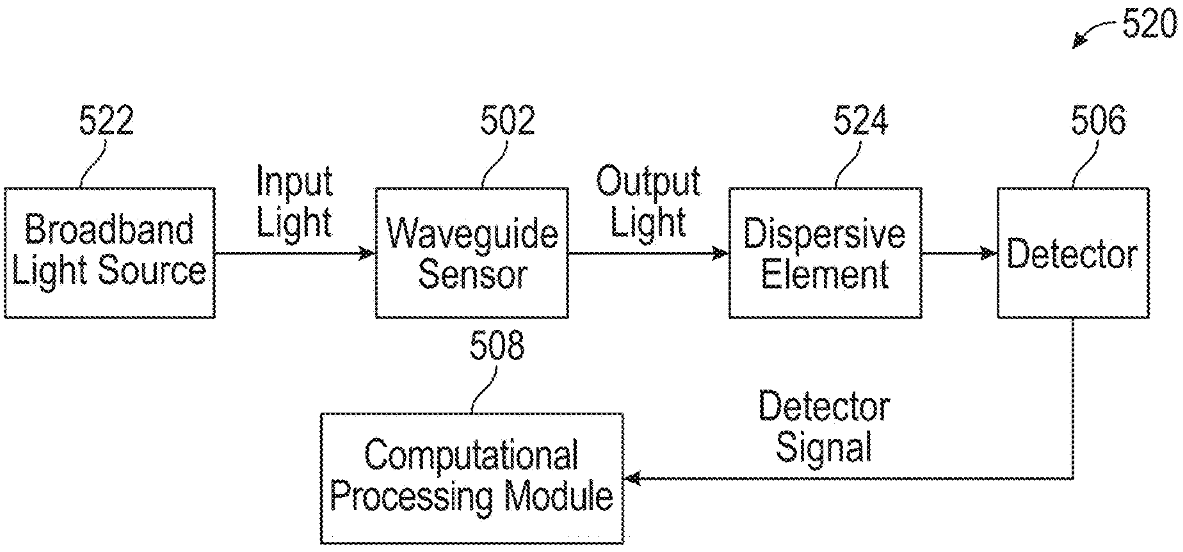

FIGS. 5A and 5B are schematic block diagrams of VOC sensing systems, in accordance with various embodiments, that incorporate the waveguide structure 100 of FIGS. 1A and 1B. Shown in FIG. 5A is a system 500 that includes, in addition to the waveguide sensor 502 (as implemented, e.g., by waveguide 102), a tunable mid-infrared light source 504 (e.g., a tunable laser), a mid-infrared detector 506, and a computational processing module 508. The light source 504 generates the optical input to the waveguide 102 by coupling light, directly or indirectly, into the waveguide 102 to launch an optical mode. The light propagates through the waveguide 102 and exits at the output, where the intensity of the optical output mode is measured by the detector 506. The computational processing module 508 processes the detector signal to determine the attenuation of the optical mode in the waveguide 102, e.g., as a function of wavelength to obtain spectral attenuation information or at a selected wavelength. The computational processing module 508 may be implemented in analog or digital circuitry; if the latter, the electronic output of the detector 506 may be converted into a digital signal by an analog-to-digital converter (not shown). In some embodiments, the computational processing module 508 is provided by a programmable processor (e.g., a field-programmable gate array (FPGA) or general-purpose central processing unit (CPU)) executing suitable software.

The light source 504 is tunable over an operating wavelength range of the sensing system 500, facilitating measurements of absorption spectra, across that wavelength range, of samples in contact with the waveguide sensor 502 and detection of analytes (including VOCs) with characteristic absorptions at wavelengths within that range. In some embodiments, the operating wavelength range extends from about 2.5 μm or less to about 15 μm or more. The detector 506 may be, for instance, a photodetector that measures the overall intensity of the light output by the waveguide sensor 502, or, alternatively, a camera (e.g., an array of photosensors) that allows imaging the optical mode at the waveguide sensor output. Either way, the detector 506 is selected or configured to be sensitive to light within the operating wavelength range. In various embodiments, for instance, an indium antimonide (InSb) infrared camera, which is responsive to light from less than 1 μm up to 5.3 μm, an HgCdTe (MCT) camera, which is sensitive up to at least 7 μm, or a pyroelectric detector, which operates at wavelengths up to at least 15 μm, is used.

The computational processing module 508 may be configured to create a spectrum by associating the measured output signal of the sensor 502 at a given time with the respective wavelength input by the light source at that time. The computational processing module 508 may have knowledge of the light-source wavelength by virtue of controlling the tunable wavelength itself, or by receiving a signal indicative of the wavelength from a separate light-source controller (not shown). In addition to computing a spectrum, the computational processing module 508 may also implement processing logic for analyzing the spectrum, e.g., based on data about the absorption characteristics of a various VOCs (e.g., as stored in memory of the computational processing module 508), to identify the types of VOCs present within the sample and/or determine their concentration. Alternatively to acquiring a spectrum by varying the wavelength with time, the system 500 can also be operated continuously at a given wavelength, e.g., corresponding to a characteristic absorption line of a certain VOC, to measure a time-resolved absorption signal indicative of a (possibly variable) concentration of the VOC in the sample.

FIG. 5B shows an alternative sensing system 520, which includes, instead of a tunable light source 504, one or more light source 522 providing broadband light (collectively)

covering the operating wavelength range. To facilitate the acquisition of a spectrum, the system 500 may further include a dispersive element 524 at the output of the waveguide sensor 502, preceding the detector(s) 506, to spatially spread out the light by wavelength. Using a camera as the detector 506; the output intensity at different wavelengths can then be measured at different respective locations within the sensor array of the camera. Alternatively to a camera, multiple photodetectors (e.g., a photodiode array detector) may be placed at different locations corresponding to different respective wavelengths, or a single detector (or camera) may be moved to measure the intensity for different wavelengths. In a broadband-light sensing system 520, the computational processing module 508 generates a spectrum by associating the location of the measured light intensity with wavelength.

In both sensing systems 500, 520, the light emitted by the light source 504, 522 may be collimated, e.g., with a refractive lens, into an optical fiber, which may then be butt-coupled to the waveguide sensor 502. Similarly, the light output by the waveguide sensor 502 may be focused by a lens (e.g., a barium fluoride biconvex lens) onto the camera or other detector 406. Alternatively, the light source 504, 522 and/or detector 506 may be implemented as photonic circuit components and monolithically integrated with the waveguide sensor 502 on the same substrate, e.g., in a semiconductor device layer (or multiple such layers) disposed above the undercladding. Lasers and detectors may be formed, e.g., by silicon device structures in conjunction with III-V structures serving as active regions and associated electrodes, which may be patterned and manufactured using standard CMOS processes; suitable photonic-component structures and manners of manufacturing same are well-known to those of ordinary skill in the art. To provide just one example, in some embodiments, a quantum cascade laser, which can emit light in the mid-infrared regime, may be used as the light source. Alternatively to creating the photonic circuit components in a separate semiconductor device layer, they may also in part be created in the chalcogenide layer disposed on the undercladding during manufacture of the waveguide sensor 502. Integrating light source, sensor, and detector on the same substrate provides a self-contained, chip-scale VOC sensor device. In some embodiments, furthermore, the computational processing module 506 is implemented, in whole or in part, by microelectronic circuitry, which is likewise capable of integration on the same chip in the semiconductor device layer. In some embodiments, such integrated microelectronic circuitry, instead of performing the signal-processing itself, includes a signal transmitter for wireless transmission of the sensor data (e.g., as captured in the photodetector output). Such data transmission enables a compact sensor device to communicate with a separate computing device, such as a general-purpose computer executing software for processing the signals.

Figure 6:
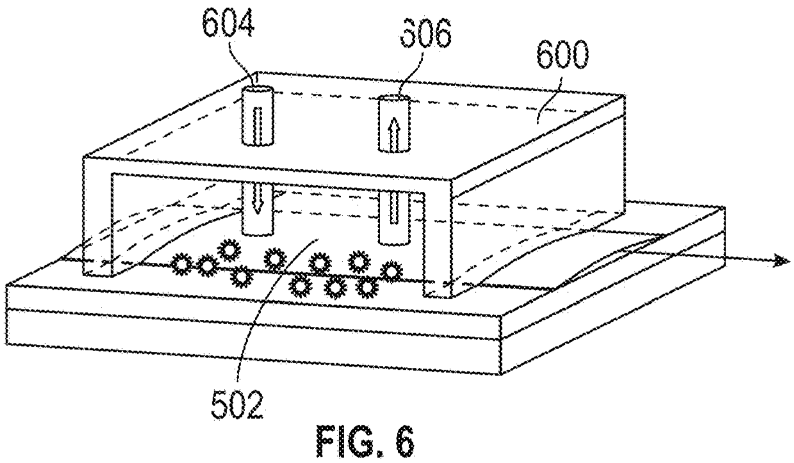
FIG. 6 is a cut-away perspective view of a waveguide sensor enclosed in a microfluid chamber, in accordance with various embodiments.

FIG. 6 is a cut-away perspective view of a waveguide sensor 502 (implemented by waveguide 102) enclosed in a microfluidic chamber 600, in accordance with various embodiments; this configuration may be used during sensor calibration as well as, optionally, for measurements in the field. The microfluidic chamber 600 may be made, e.g., of polydimethylsiloxane (PDMS) or some other organosilicon, using micro-fluidic or opto-fluidic chip manufacturing techniques known to those of ordinary skill in the art. The microfluidic chamber 600 includes an inlet 604 and an outlet 606 through which a gas flow through the chamber 600 and across the waveguide sensor 502 can be established. During sensor calibration, a mixture of VOC vapor and a diluting gas (e.g., nitrogen ($N_2$) gas), is delivered to the microfluidic chamber 600, where the waveguide sensor 502 is exposed to the analytes. Different VOC concentrations can be achieved by regulating relative flow rates of the VOC and diluting gas. As the waveguide sensor 502 is exposed to the VOCs, the optical output mode intensity is monitored, using system components as described above with respect to FIGS. 5A and 5B.

Figure 7:
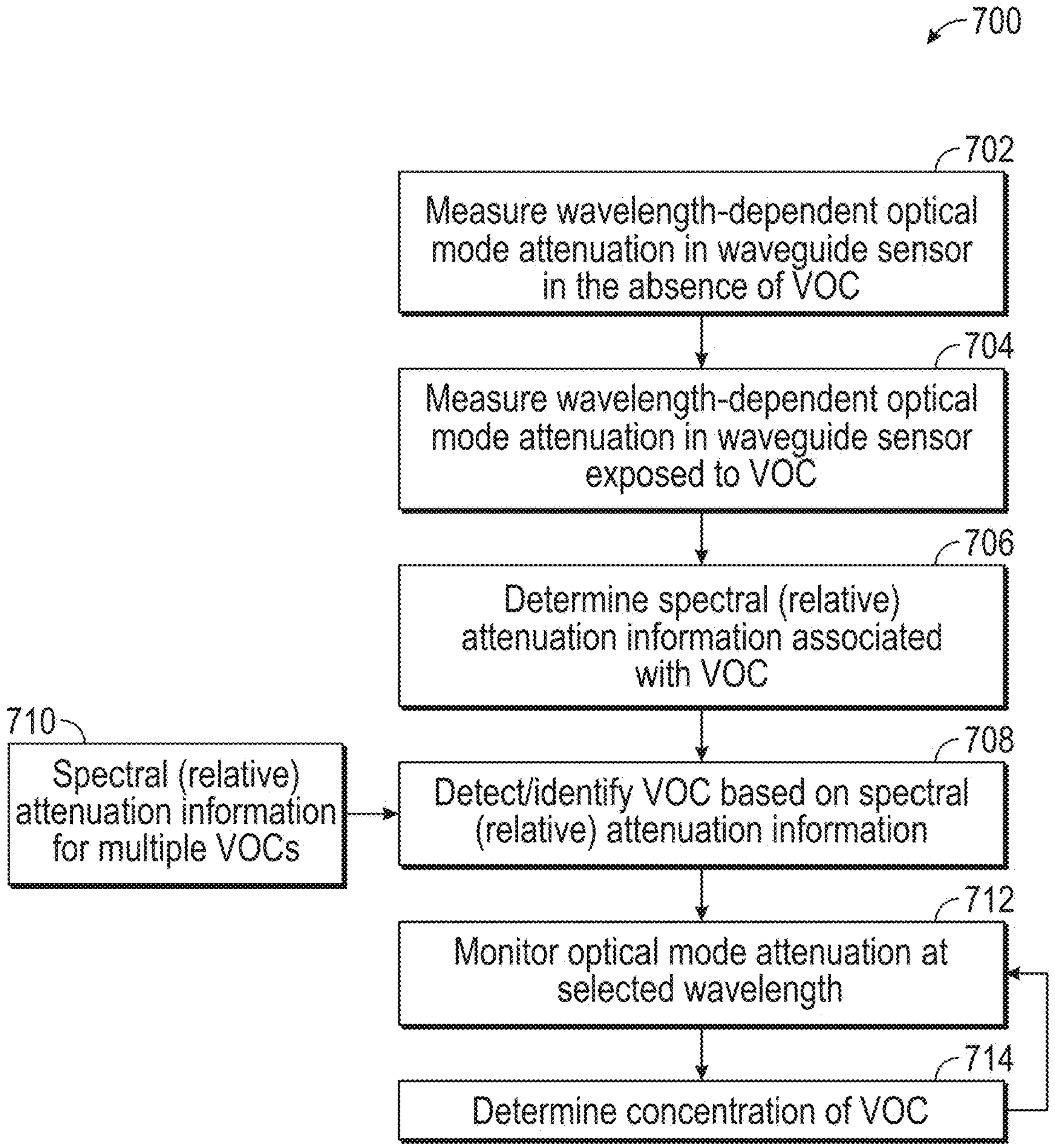
FIG. 7 is a flow chart of a method for VOC sensing in accordance with various embodiments.
Figure 8A:
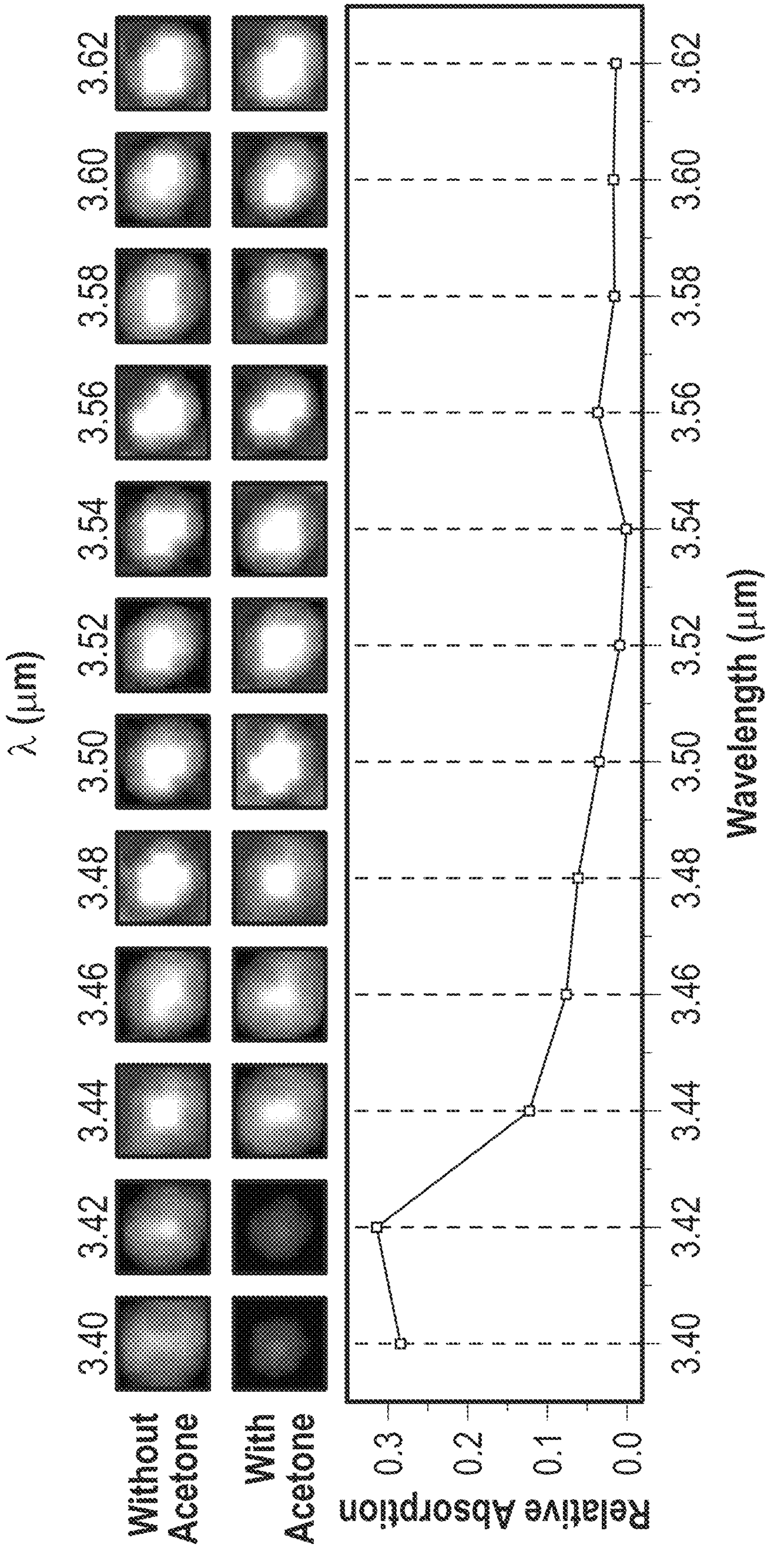
FIG. 8A is a graph of the relative absorption by acetone as measured with an example $As_2Se_3$ waveguide sensor according to FIGS. 1A and 1B over a range of mid-infrared wavelengths, along with two-dimensional optical model profiles.
Figure 8B:
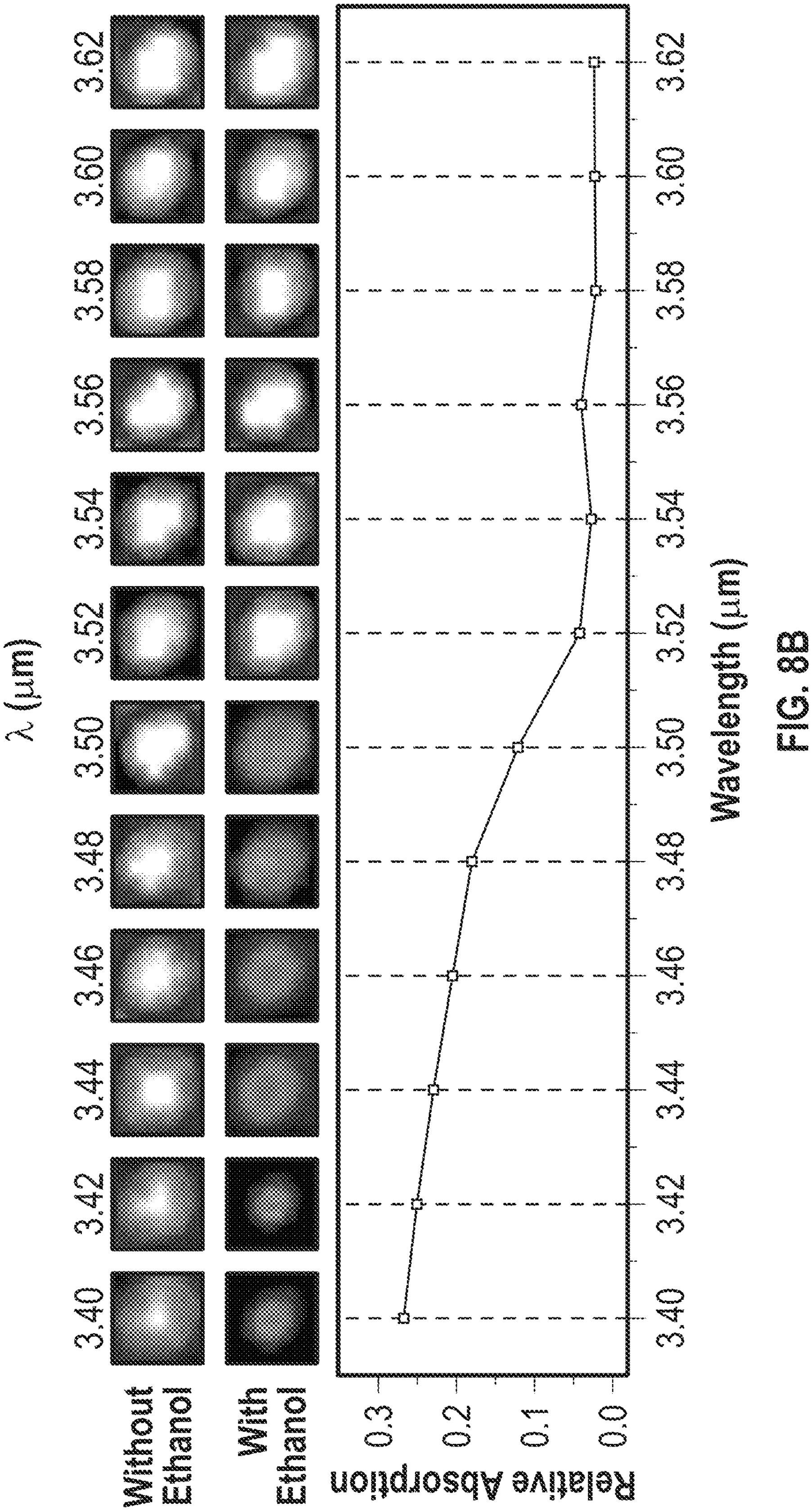
FIG. 8B is a graph of the relative absorption by ethanol as measured with the example $As_2Se_3$ waveguide sensor according to FIGS. 1A and 1B over a range of mid-infrared wavelengths, along with two-dimensional optical model profiles.

FIG. 7 is a flow chart of a method 700 for VOC sensing in accordance with various embodiments. The method 700 involves measuring the attenuation of an optical mode in a chalcogenide waveguide sensor by coupling infrared light from a light source into the waveguide to launch an optical mode (e.g., the fundamental transverse mode) and measuring the intensity of the optical mode at the waveguide output. Optical mode attenuation is measured as a function of wavelength (over a range within the mid-infrared regime) while the waveguide sensor is exposed to a VOC (act 704) to determine spectral attenuation information associated with the VOC (act 706). In some embodiments, the optical mode attenuation is also measured, for comparison, in the absence of the VOC (act 702), allowing relative attenuation information to be determined (in act 706). Such relative attenuation information may be, e.g., the relative absorption, which is defined as the normalized difference between the output mode intensities $I_0$ and $I_F$, respectively, before and after VOC exposure of the waveguide: $A=(I_0-I_F)/I_0$; or the relative intensity, which is defined as $I=1-A$. The spectral (relative or absolute) attenuation information generally differs between different compounds, and thus provides a means to identify and discriminate between compounds based on their associated spectral absorption characteristics. Accordingly, in various embodiments, spectral (e.g., relative) attenuation information 710 is measured for multiple VOCs and stored (e.g., in computer memory) for later retrieval and comparison, to facilitate identifying VOCs among multiple VOCs or chemical compounds in general. FIGS. 8A and 8B, described below, provide examples of such compound-specific absorption characteristics.

For a given detected VOC, the method 700 may further include, in act 712, measuring or monitoring optical mode attenuation (e.g., in terms of a relative absorption or intensity) at a selected wavelength (e.g., a wavelength within a strong absorption band of the VOC) to determine the VOC concentration or concentration changes over time (714). The concentration-dependent attenuation of the optical mode in the waveguide sensor can, for this purpose, be calibrated, e.g., using the set-up shown in FIG. 6. Such monitoring can, in some embodiments, be performed in real time or near real time.

FIGS. 8A-9C illustrate various VOC measurements with an example chalcogenide waveguide, characterizing the capabilities of waveguide-based VOCs in accordance with some embodiments. The example sensing waveguide used in these measurements was made of $As_2Se_3$ (on an $SiO_2$ undercladding) and had a flattened semi-elliptical cross-sectional profile about 10 μm wide and 1.5 μm thick. The waveguide featured a smooth exposed waveguide surface without bumps, indentations, or sharp edges; a sharp interface between the $As_2Se_3$ and $SiO_2$ layers; and a homogeneous material composition across the film surface and along the film depth. The high degrees of surface smoothness and material uniformity minimized optical losses due to scattering at surface features and refractive-index variations and, along with a high refractive index contrast between waveguide and undercladding, achieved efficient light wave guiding. Mode intensity measurements at different waveguide lengths revealed optical losses of about 0.16 dB/cm, which is comparable with reported waveguide-based sensors for other chemical compounds.

FIGS. 8A and 8B illustrate the sensitivity and specificity of the waveguide sensor to acetone and ethanol, respectively. For the depicted measurements, the wavelength of a tunable light source was sequentially scanned from 3.4 μm to 3.62 μm because this spectral range overlaps with the characteristic absorption bands caused by the C—H functional group. FIG. 8A shows the two-dimensional optical mode profiles at discrete wavelengths within this range, measured both in the absence (first row) and in the presence (second row) of acetone. Also shown is the relative absorption computed from the mode profiles with and without acetone, which is plotted as a function of wavelength and correlated with respective pairs of mode profiles. As can be seen, a bright and sharp optical mode was observed from 3.4 μm to 3.6 μm before any chemical was present. Upon exposure of the waveguide sensor to acetone (as acetone vapor was injected into a PDMS chamber enclosing the waveguide sensor), the mode intensity sharply decreases at 3.40 μm to 3.42 μm. The characteristic absorption associated with acetone was clearly observed at 3.40 μm to 3.44 μm.

For comparison, FIG. 8B shows the two-dimensional optical mode profiles measured in the absence (first row) and in the presence (second row) of ethanol, along with a graph of the relative absorption derived from the mode profiles. When ethanol vapor was injected into the PDMS chamber, the mode intensity decayed over a broad spectrum from 3.40 μm to 3.52 μm, reflecting that the absorption band of ethanol is wider than that of acetone. Thus, the chalcogenide sensor was shown to be able to differentiate ethanol and acetone vapor by their distinct mid-infrared C—H absorption.

Figure 9A:
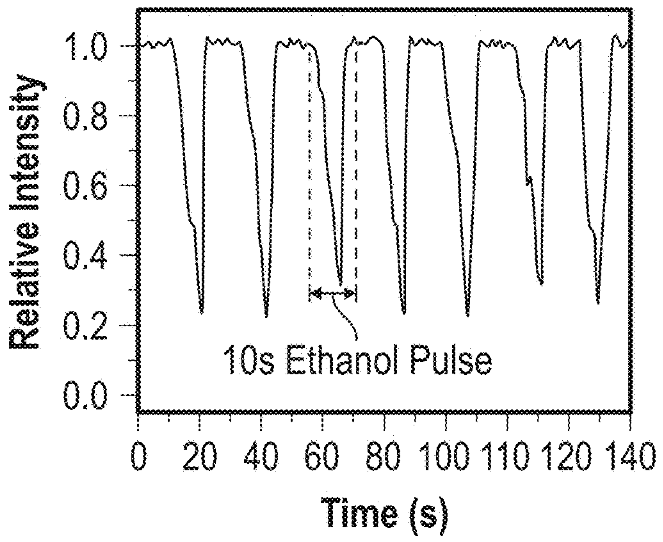
FIG. 9A is a graph illustrating the transient response of the example $As_2Se_3$ waveguide sensor according to FIGS. 1A and 1B to ethanol during pulsed ethanol exposure.
Figure 9B:
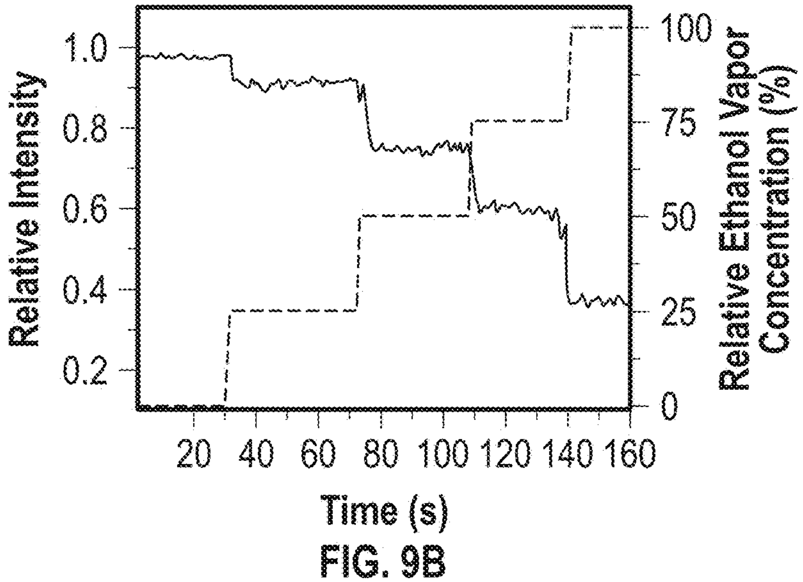
FIG. 9B is a graph illustrating the transient response of the example $As_2Se_3$ waveguide sensor according to FIGS. 1A and 1B to stepwise increases in ethanol concentration.
Figure 9C:
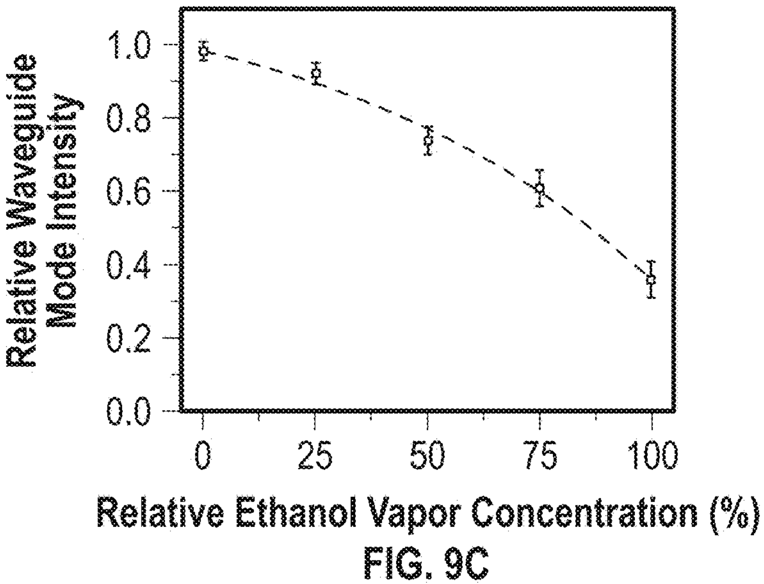
FIG. 9C is a graph illustrating the dependence of the relative waveguide mode intensity of the example $As_2Se_3$ waveguide sensor according to FIGS. 1A and 1B on ethanol concentration.

FIGS. 9A-9C illustrate the ability of the waveguide sensor to monitor ethanol (as an example of a VOC) concentrations in (near) real time. For purposes of characterizing the real-time sensing performance, the diluting gas (99.999% $N_2$) was mixed with ethanol vapor at different gas flow rates. The laser wavelength was tuned to 3.46 μm, aligned with the characteristic ethanol C—H absorption, to continuously trace the ethanol concentration. FIG. 9A is a graph showing the transient response of the waveguide sensor, in terms of the relative intensity of the output mode, to a sequence of ten-second ethanol vapor pulses injected into the PDMS chamber. As can be seen, the output mode intensity dropped abruptly whenever the waveguide sensor was exposed to ethanol. Once the ethanol was purged from the chamber by injecting $N_2$, the light intensity recovered to the original level. During ethanol vapor monitoring, a fast response of less than five seconds was observed; this response is attributable to the high sensitivity of mid-infrared detection as well as the small gas chamber volume.

To quantitatively correlate the mode intensity variation with ethanol vapor concentration, ethanol vapor with concentrations of 0%, 25%, 50%, 75%, and 100% in $N_2$ was sequentially injected int to the PDMS chamber. FIG. 9B is a graph illustrating the transient response of the waveguide sensor to these stepwise increases in ethanol concentration. As shown, the light intensity decreased as the ethanol vapor concentration increased. By fitting the intensity and concentration plot, a monotonic dependence of the relative waveguide mode intensity on ethanol concentration was observed; this dependence is plotted in FIG. 9C.

Although embodiments have been described with reference to specific example embodiments, it will be evident that various modifications and changes may be made to these embodiments without departing from the broader scope of the invention. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This description, therefore, is not to be taken in a limiting sense, and the scope of various embodiments is defined only by the appended claims, along with the full range of equivalents to which such claims are entitled.

What is claimed is:

1. A method of manufacturing a chalcogenide waveguide on an undercladding of a substrate, an exposed surface of the waveguide being free of edges, the method comprising:
- negatively defining a layout of the waveguide by photolithographically patterning a photoresist layer deposited on the undercladding;
- depositing a chalcogenide layer over the patterned photoresist layer by rotational sputtering, wherein the substrate is tilted or off-set relative to a chalcogenide sputtering target and is further continuously rotated; and
- lifting off the photoresist layer.

2. The method of claim 1, wherein a tilt angle of the substrate relative to the chalcogenide sputtering target is between 15 and 75 degrees.

3. The method of claim 1, wherein:
- the substrate is continuously rotated about a first axis perpendicular to the substrate, and
- sputtered particles emanate from the sputtering target anisotropically with rotational symmetry about a second axis normal to the sputtering target and with maximum particle density along the axis.

4. The method of claim 3, wherein the first axis and the second axis enclose an angle between 15 and 17 degrees.

5. The method of claim 3, wherein the first axis and the second axis are parallel and offset relative to each other.

6. The method of claim 5, wherein a connecting line between a point where the first axis intersects the substrate and a point where the second axis intersects the sputtering target encloses an angle between 15 and 17 degrees with the first and second axes.

7. The method of claim 1, further comprising, prior to defining the layout of the waveguide, providing, as the substrate, a silicon waver with a layer of oxide serving as the undercladding, and depositing the photoresist layer on the undercladding.

8. The method of claim 1, wherein the photoresist layer comprises negative tone photoresist NR9-3000PY.

9. The method of claim 1, wherein the sputtering target is a 99.99% arsenic triselenide target.

10. The method of claim 1, wherein the rotational sputtering comprises radio-frequency sputtering.

11. The method of claim 10, wherein the radio-frequency sputtering takes place at a power of 40 W.

12. The method of claim 1, wherein the undercladding comprises oxide or fluoride.

13. The method of claim 1, wherein the chalcogenide waveguide remaining on the undercladding following the lifting off of the photoresist layer has a width-to-height aspect ratio of at least 2.

14. The method of claim 1, wherein the chalcogenide waveguide remaining on the undercladding following the lifting off of the photoresist layer has a width of about 10 μm as measured between points of half-maximum height, and a height of about 1.5 μm.

15. The method of claim 1, wherein the chalcogenide waveguide remaining on the undercladding following the lifting off of the photoresist layer has flattened semi-elliptical profile.

16. A sensor device for detecting volatile organic compounds, the sensor device comprising:

a substrate comprising an undercladding; and a chalcogenide waveguide created on the undercladding by a process comprising:

negatively defining a waveguide layout by photolithographically patterning a photoresist layer deposited on the undercladding, depositing chalcogenide over the patterned photoresist layer by sputtering while the substrate is continuously rotated and is tilted or off-set relative to a chalcogenide sputtering target, and lifting off the photoresist layer.

17. The sensor device of claim 16, wherein tilting or off-setting the substrate relative to the sputtering target produces a smooth top surface of the waveguide, free of edges.

18. The sensor device of claim 16, wherein tilting or off-setting the substrate relative to the sputtering target produces width-to-height aspect ratio of a cross section of the chalcogenide waveguide that is at least two.

19. The sensor device of claim 16, wherein, in the process for creating the chalcogenide waveguide on the undercladding, the substrate is titled relative to the chalcogenide sputtering target by between 15 and 75 degrees.

20. The sensor device of claim 16, wherein, in the process for creating the chalcogenide waveguide on the undercladding, an axis of rotation of the substrate is parallel to and offset relative to an axis of rotational symmetry of particles emanating from the sputtering target.

* * * * *